United States Patent [19]

Kraus et al.

[11] Patent Number: 5,304,134
[45] Date of Patent: Apr. 19, 1994

[54] LUBRICIOUS YET BONDABLE CATHETER CHANNEL SLEEVE FOR OVER-THE-WIRE CATHETERS

[75] Inventors: Jeff L. Kraus; Nitin Matani, both of San Jose, Calif.

[73] Assignee: Danforth Biomedical, Inc., Menlo Park, Calif.

[21] Appl. No.: 822,291

[22] Filed: Jan. 17, 1992

[51] Int. Cl.⁵ .................................................. A61M 29/00
[52] U.S. Cl. ..................................... 604/96; 606/194
[58] Field of Search ............... 604/282, 280, 265, 96, 604/264, 93, 104, 266; 606/194

[56] References Cited

U.S. PATENT DOCUMENTS

| | | | |
|---|---|---|---|
| 4,563,181 | 1/1986 | Wijayarathna et al. | 604/280 |
| 4,782,834 | 11/1988 | Maguire et al. | 604/280 |
| 4,863,424 | 9/1989 | Blake, III et al. | 604/282 |
| 4,898,591 | 2/1990 | Jang et al. | 604/282 |
| 4,950,257 | 8/1990 | Hibbs et al. | 604/265 |
| 4,981,478 | 1/1991 | Evard et al. | 604/282 |
| 5,100,381 | 3/1992 | Buns | 606/194 |
| 5,120,323 | 6/1992 | Schokey et al. | 606/194 |

FOREIGN PATENT DOCUMENTS

0279959 12/1987 European Pat. Off. .... A61M 25/00

*Primary Examiner*—C. Fred Rosenbaum
*Assistant Examiner*—Manuel Mendez
*Attorney, Agent, or Firm*—Townsend and Townsend Khourie and Crew

[57] ABSTRACT

The inner tubular element of an annular over-the-wire dilatation balloon catheter defines the guidewire lumen extending through the catheter shaft and the balloon and is bonded to the balloon at the distal opening of the balloon. In accordance with the invention, the inner tubular element is constructed in two segments. The proximal segment is constructed of a polymer such as polyethylene which has a lubricious surface, while the distal segment is constructed of a polymer such as nylon, polyurethane, or a nylon/polyurethane blend, which lacks lubricity but forms a secure bond with the balloon at the distal opening. The bond by which the proximal and distal segments are joined is thus removed from the distal balloon opening, and accordingly less susceptible to failure upon pressurization of the balloon.

10 Claims, 3 Drawing Sheets

LUBRICIOUS YET BONDABLE CATHETER CHANNEL SLEEVE FOR OVER-THE-WIRE CATHETERS

This invention relates to guidewires for medical catheters and to catheter-guidewire systems, and in particular to catheter-guidewire systems known as "exchangeable" or "over-the-wire" systems.

BACKGROUND OF THE INVENTION

Percutaneous guidewire-directed catheters of many different types are used in a wide variety of medical procedures. These types include angioscopic catheters, angioplasty catheters, and genito-urinary catheters; some are intended for diagnostic purposes, some for dilatation purposes, and some for purposes of delivering a drug, contrast agent or other useful agent to an internal bodily vessel.

These various types of catheters contain numerous features affecting their ease and effectiveness of use. These features are most conveniently understood by examination of a single class of catheters—i.e., dilatation balloon catheters for angioplasty procedures. The following discussion will therefore focus on this one class, with the understanding however that the scope of this disclosure extends well beyond this class to encompass all guidewire-directed catheters.

In recent years, angioplasty has gained widespread acceptance and use as a technique for treating atherosclerotic coronary and peripheral vascular diseases. According to this technique, a dilatation balloon catheter-guidewire system is percutaneously introduced into the patient's vasculature under fluoroscopic control until the balloon component of the system spans the confines of a vascular stenosis. Once in position, the balloon is inflated by hydraulic pressure to dilate the stenosis and thereby relieve the obstruction to blood flow.

A feature of certain catheter-guidewire systems which is of considerable advantage in angioplasty procedures is "exchangeability." This is the ability of the guidewire and the catheter body to be separated while inside the vasculature for purposes of removing one or the other and replacing the removed component with a substitute component which differs in some respect. The need for such an exchange arises when a component originally placed inside the vasculature is discovered subsequent to its placement to be inadequate or inappropriate for a particular stenosis. Systems having the capability of this exchange are termed "exchangeable" systems, and those in which the catheter body can be exchanged without removing the guidewire are termed "over-the-wire" systems. In exchangeable systems, either the catheter body, the guidewire or both can be replaced without the need to reestablish intraluminal access. This saves time and, in so doing, lowers the risk of patient injury due to prolonged interference with the patient's blood flow from the presence of the catheter in the vasculature. Because of this advantage as well as their inherently greater steerability, exchangeable systems command approximately 80% of the angioplasty catheter market.

While non-exchangeable systems can be constructed with single lumens, all exchangeable, and particularly over-the-wire, systems in current use contain at least two lumens, one for the guidewire and the other for the inflation fluid used to inflate the balloon. The guidewire lumen provides the guidewire with full mobility relative to the catheter body and vice versa while preventing loss of inflation fluid from both the balloon and the inflation lumen which supplies the fluid under pressure to the balloon. In some constructions, the inflation lumen is an annular lumen surrounding the guidewire lumen, whereas in others the two are side by side.

The presence of multiple lumens gives over-the-wire systems a larger cross section, however, raising the degree to which the system will impair the flow of blood and other fluids through the vasculature. This raises the risks of ischemia, of compromising the resolution of intraoperative angiography, and of interference with the intraoperative administration of therapeutic agents. For this reason, both lumens as well as the overall profile of the catheter body are designed to have as small a cross section as possible.

The development of new materials for the catheter body has led to considerable reductions in the catheter body cross section. These materials permit thinner walls and smaller caliber channels without loss of strength, function or structural integrity. There is a limit to how much the inner diameter of the guidewire channel can be reduced, however. One reason among several is that the distal segment of the guidewire is covered with a coil to provide this segment with the combination of structural strength and flexibility it needs for steering through the vasculature. While the diameter of the coil may be the same as or small than that of the proximal, full-diameter portion of the guidewire which is not covered by the coil, the coil most often limits the degree to which the diameter of the guidewire and hence the diameter of the guidewire lumen can be reduced.

Friction between the guidewire and the inner wall of the guidewire lumen is also a problem. With long guidewires and narrow lumens, it is particularly difficult in many cases to advance the catheter body over the guidewire.

Small caliber tubing may be constructed of lubricious materials such as polytetrafluoroethylene or polyethylene, which suggests the possibility of using such tubing as the guidewire lumen, while the annular space between the tubing and the catheter body serves as the inflation lumen. This is not a suitable arrangement, however, since it requires that the lubricious tubing be bonded to the balloon at the distal balloon orifice. Lubricious materials do not bond well to other materials, and as a result the bond will not be a strong one. A strong bond is indeed needed at this location, since the pressure in the balloon would otherwise tend to separate the balloon from the tubing. Failure of the bond in this manner would result in escape of the inflation fluid into the vasculature.

For these and other reasons, there exists a need for a catheter body for over-the-wire catheters which contains tubing for the guidewire lumen which is both lubricious and capable of bonding securely to the balloon.

SUMMARY OF THE INVENTION

In accordance with this invention, the inner tubular element which separates the axial and annular passages of the catheter which serve as the guidewire and inflation lumens, respectively, is in two parts. The first is a proximal segment formed of a lubricious polymer, and the second is a distal segment formed of a polymeric material which is less lubricious than that of the proximal segment and is capable of bonding strongly to the balloon orifice. The lubricious tubular segment is thus bonded not to the balloon but to the less lubricious distal tubular segment, and the two will not be forced apart when the inflation lumen and balloon are pressurized. In preferred embodiments of the invention, the joint between the two segments is an overlap which is even less likely to separate.

The lengths of the two segments are such that when the catheter is fully advanced over the guidewire, and likewise when the guidewire is fully inserted in the catheter, the distal segment of the inner tubular element extends proximally no further than the coiled distal segment of the guidewire. The lubricious segment of the tubular element is therefore long enough to cover the entire length of the smooth-surfaced section of the guidewire.

The coiled segment of the guidewire, due to its irregular surface, offers less surface contact, and hence less friction, with the inner surface of the tubular element than does the smooth segment of the guidewire. In procedures where the guidewire is exchanged without removing the catheter from the vasculature, only the coiled segment of the guidewire enters the distal, less lubricious segment of the tubular element. Conversely, in procedures where the catheter is exchanged without removing the guidewire from the vasculature, the distal, less lubricious segment of the tubular element will pass over the smooth-surfaced segment of the guidewire. The fact that this less lubricious material constitutes only a portion of the tubular element, however, the remainder being the lubricious material, results in a considerable reduction in friction relative to tubular elements which do not include lubricious materials at all.

In either case, particularly in procedures involving exchange of the catheter by advancement of the catheter over the guidewire, the shorter the distal, less lubricious segment of the tubular element is, the less friction there will be between the catheter and the guidewire. Preferably, the distal segment of the tubular element is no longer than the length of the balloon, the joint between the segments thus being either at the proximal end of the balloon or within the balloon interior.

Other advantages, aspects and features of preferred embodiments of the invention will be apparent from the description which follows.

DETAILED DESCRIPTION OF THE INVENTION AND PREFERRED EMBODIMENTS

Figure 1:
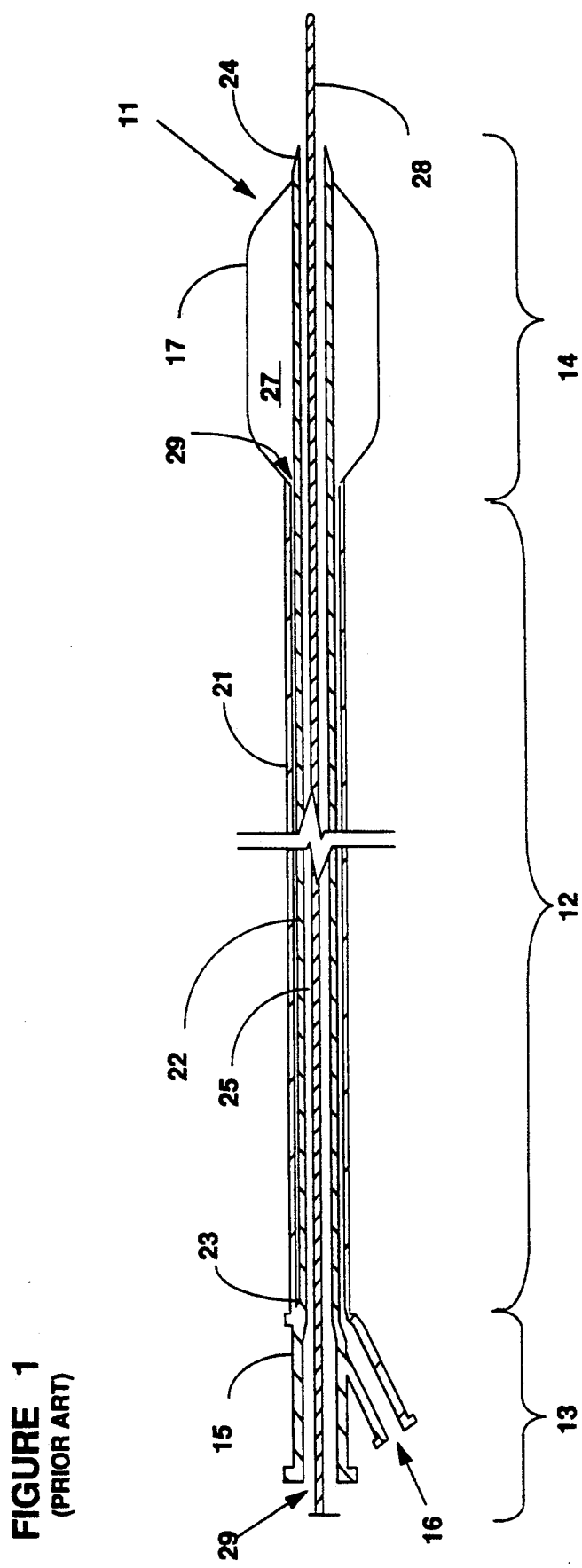
FIG. 1 is a longitudinal cross section of a catheter/guidewire system in accordance with the present invention.

The proximal segment of the inner tubular element which forms the guidewire lumen in accordance with this invention is constructed of a polyolefin with a lubricious surface. Examples of polyolefins of this nature are polyethylene, polypropylene and poly-1-butene. The preferred polyolefin is polyethylene, particularly high-density polyethylene.

The distal segment of the inner tubular element is formed of a polymeric material which bonds strongly to the balloon. The balloon is itself a polymeric material, preferably a polyester, a prominent example of which is polyethylene terephthalate. The balloon may also be a polyethylene terephthalate blend, such as a blend of polyethylene terephthalate and a nylon, or any relatively non-compliant material. Polymeric materials which bond effectively to the balloon include such materials as polyamides, flexible polyesters, polyurethanes and various polymers based on these materials, such as derivatives, modified versions of these polymers, and blends.

Preferred polyamides are nylons, such as nylon 66, nylon 610, nylon 612, nylon 11, nylon 12 and nylon 6, as well as copolymers such as copolymers of nylon 6 and nylon 66.

Preferred polyurethanes are polyether-based polyurethanes. The polyurethanes may be prepared from diisocynates such as 1,4-diisocyanatobenzene (PPDI), toluene diisocyanate (2,4 and 2,6 blend) (TDI), 4,4'-methylenebis(phenyl isocyanate) (MDI), polymethylene polyphenyl isocyanate (PMDI), 1,5-naphthalene diisocyanate (NDI), bitolylene diisocyanate (TODI), m-xylylene diisocyanate (XDI), hexamethylene diisocyanate (HDI), 1,6-diisocyanato-2,2,4,4-tetramethylhexane (TMDI), 1,6-diisocyanato-2,4,4-trimethylhexane (TMDI), 1,4-cyclohexanyl diisocyanate (CHDI), 1,4-bis(isocyanatomethyl)cyclohexane (BDI), 1,3-bis-(isocyanatomethyl)cyclohexane ($H_6$XDI), isophorone diisocyanate (IPDI), and 4,4'-methylenebis(cyclohexyl isocyanate) ($H_{12}$MDI). Examples of polyethers used in the preparation of these polyurethanes are poly(ethylene glycol) (PEG), poly(propylene glycol) (PPG), random and block copolymers of PEG and PPG, poly(tetramethylene glycol) (PTMG), glycerol adducts, trimethylolpropane adducts, pentaerythritol adducts, ethylenediamine adducts, phenolic resin adducts, diethylenetriamine adducts, sorbitol adducts and sucrose adducts.

Examples of flexible polyesters are polyalkylene terephthalates such as poly(ethylene terephthalate) and poly(butylene terephthalate), as well as blends, derivatives and block copolymers of these polymers. One specific example is Hytrel (DuPont), which is a block copolymer of poly(tetrahydrofuran) and poly(butylene terephthalate).

Blends of polyamides and polyurethanes, and particularly blends of nylons and polyether-based polyurethanes, are particularly preferred. An example presently preferred is a commercially available resin bearing the tradename "Pebax," obtainable from ATOCHEM INC., Polymers Division, Glen Rock, N.J.

The bond between the distal segment of the inner tubular element and the catheter balloon is at the distal end of the balloon, the bond sealing the distal orifice of the balloon around the exterior surface of the distal end of the tubular segment. The bond may be formed by any conventional adhesive for bonding polymers. The optimal adhesive in any particular example may vary with the tubing and balloon materials, as one skilled in the art will appreciate. Examples of suitable adhesives are those cured by ultraviolet light. A presently preferred example is an adhesive bearing the tradename DYMAX, available from Dymax Corporation, Torrington, Conn., U.S.A.

A conventional adhesive may also be used for the bond between the proximal (lubricious) and distal segments of the inner tubular element. By virtue of its location, the bond is less susceptible to failure during inflation of the balloon, since the force exerted by the inflation pressure will not tend to separate the two segments, particularly with the guidewire extending through both whereupon the force will tend to compress both segments toward the guidwire. In preferred embodiments of the invention, the bond is formed by overlapping the inner ends of the two segments for a distance of about 1-10 mm, preferably about 8-9 mm, with the adhesive in between the overlapping segments.

As an alternative to the use of an adhesive, the proximal and distal segments of the inner tubular element may also be joined by expanding and shrinking one segment over the other to form a lap joint. This may be done by first irradiating the tip of one of the segments, preferably the proximal segment, with an electron beam or with gamma radiation to produce cross-linking in the polymer, then heating and pressurizing the tip to expand it, inserting the tip of the other segment, and finally heating the irradiated segment whereupon it will shrink back to its original diameter and tightly adhere to the other segment.

The location of the joint between the two segments may vary, and is not critical. To serve its purpose, the proximal (lubricious) segment of the inner tubular element will be long enough to impart a sufficiently lubricious effect to the tubular element as a whole, such that movement of the catheter over the guidewire, or the guidewire into the catheter, will have the benefit of the lubricity. The distal (balloon-bondable) segment may thus be extremely short without compromising its function.

As is well known among those with experience in the manufacture and use of dilatation balloon catheters, particularly catheters intended for use in angioplasty, most guidewires are formed of a smooth-surfaced rod except for a segment at the distal end, whose outer surface is defined by a tightly coiled wire. The coil has the same outer diameter as the proximal segment of the guidewire, and encircles a central rod of a smaller diameter, the central rod being a tapered-down extension of the proximal segment of the guidewire. The length of the coil is approximately 30 cm. Its purpose is to provide the guidewire with flexibility, or the ability to be maneuvered through the convoluted passageways in the vasculature to reach the stenosis without puncturing the blood vessel wall, and yet to provide the guidewire with sufficient bulk and structural integrity to permit manipulation of the guidewire from the proximal end of the catheter. In other guidewires, the distal end is covered by a flexible polymeric sheath, which serves the same purpose as the coil.

Whether the distal segment of the guidewire has a coil or a polymeric sheath as its outer surface, there is less friction between this segment of the guidewire and the inner tubular element than there is at the proximal segment of the guidewire whose surface is the relatively smooth metal surface of the mandrel. For coil-surfaced guidewires, only the radial extremities of the coil surface will contact the tubular element, thereby providing less contact surface for friction than the mandrel. For polymer-sheathed guidewires, the polymer itself is generally more lubricious than the metallic surface of the mandrel. In either case, the distal, less lubricious segment of the inner tubular element in optimal implementations of the invention is no longer in length than the distal, relatively low-friction segment of the guidewire.

As is known among those skilled in the art, the guidewire and catheter are generally constructed such that a terminal portion of the guidewire protrudes through the distal end of the balloon when the two parts are assembled in their final positions for use in an angioplasty procedure. This protruding terminal portion is generally about 3 cm in length. Hence, it is preferred that the distal, less lubricious segment of the inner tubular element be no longer than the length of the distal, relatively low-friction segment of the guidewire less the length of protruding terminal portion. Hence, the maximum length of the distal, less lubricious segment of the tubular element is a maximum of about 27 cm in length, and the joint between the two segments is consequently a distance of at most about 27 cm from the distal end of the balloon.

In the most preferred embodiments of the invention, the joint is located within the confines of the balloon, just inside the proximal end.

Turning now to the Figures, FIG. 1 illustrates an over-the-wire catheter/guidewire system 11. The catheter portion includes a shaft 12, a proximal end 13 and a distal end 14. The proximal end 13 has an adapter 15 which has a side port 16 through which hydraulic pressure is conveyed for purposes of inflation of the balloon, whereas the distal end 14 contains the balloon 17.

The shaft 12 of the catheter includes an outer tubular element 21 and an inner tubular element 22. The proximal end 23 of the inner tubular element 22 is mounted to the proximal end of the shaft 12. The inner tubular element 22 extends through the balloon 17, and the distal end 24 of the inner tubular element is mounted to the distal end of the balloon 17. The outer tubular element 21 and inner tubular element 22 define two lumens, an axial lumen 25 for passage of the guidewire, and an annular lumen 26 which communicates the interior 27 of the balloon with the side port 16 in the proximal adapter 15. Occasionally, over-the-wire catheters are constructed with three lumens, the third serving as a air vent for the balloon. The embodiment shown in this Figure, however, contains only two. The guidewire lumen 25 and the inflation lumen 26 are isolated from each other so that the balloon can be inflated without leakage of inflation fluid into the guidewire lumen. The guidewire 28, whose distal segment may be either coil-surfaced or polymer-sheathed, extends from an axial port 29 in the proximal adapter, through the guidewire lumen 25, and out the distal end of inner tubular element 22 to protrude from the distal end of the balloon 17.

Figure 2:
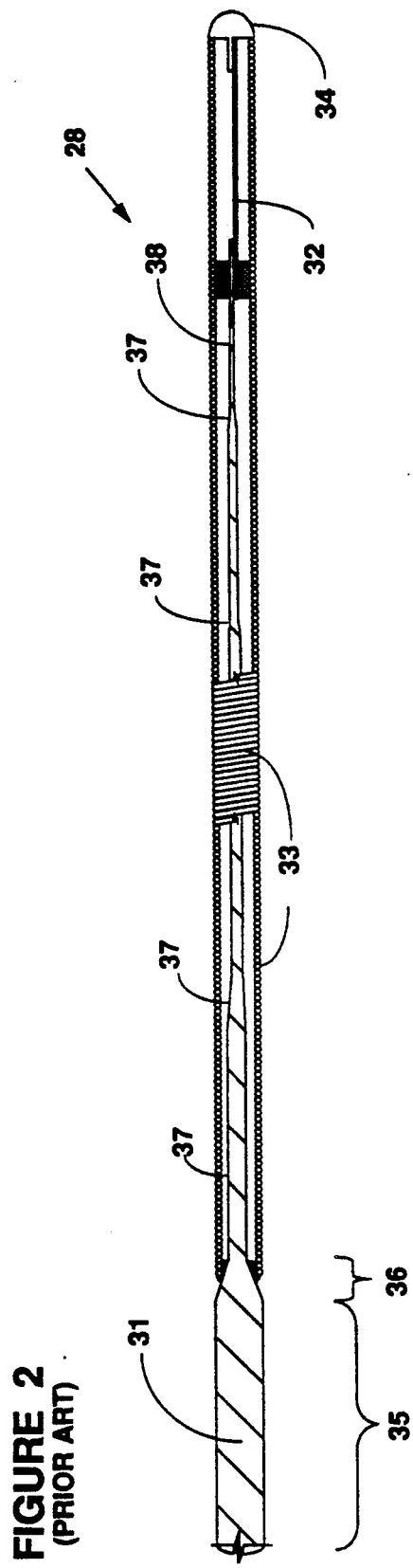
FIG. 2 is a longitudinal cross section of a guidewire for use in conjunction with a catheter body in accordance this invention.

FIG. 2 illustrates in detail a typical guidewire 28 with a coil-surfaced distal segment. The components of the guidewire are a mandrel 31, a shaping ribbon 32, a coil 33 and a tip 34 at the distal end. The mandrel 31 is a solid metallic rod, generally stainless steel, of circular cross section. The proximal portion 35 of the mandrel is a full-profile section and extends to the proximal end of the guidewire. The proximal end of the coil 33 is joined to the mandrel at a tapered section 36 on the mandrel by conventional means such as a solder joint. In this particular guidewire, the outer diameter of the coil is equal to the outer diameter of the full-profile section of the mandrel proximal to the tapered section 36, although in other coil-surfaced guidewires, the coil diameter may be less than that of the proximal section of the mandrel. From the tapered section 36 to which the proximal end of the coil is secured, the mandrel is further reduced in diameter by a series of additional tapers 37, which impart successively increasing flexibility to the mandrel. The lowest profile section 38 is joined to the shaping ribbon 32, which is a curved planar ribbon which is highly flexible but returns to its curved configuration (perpendicular to the plane of the Figure) when at rest. The tip 34 of the guidewire is a solder joint which joins the shaping ribbon 32 to the coil 33.

Figure 3:
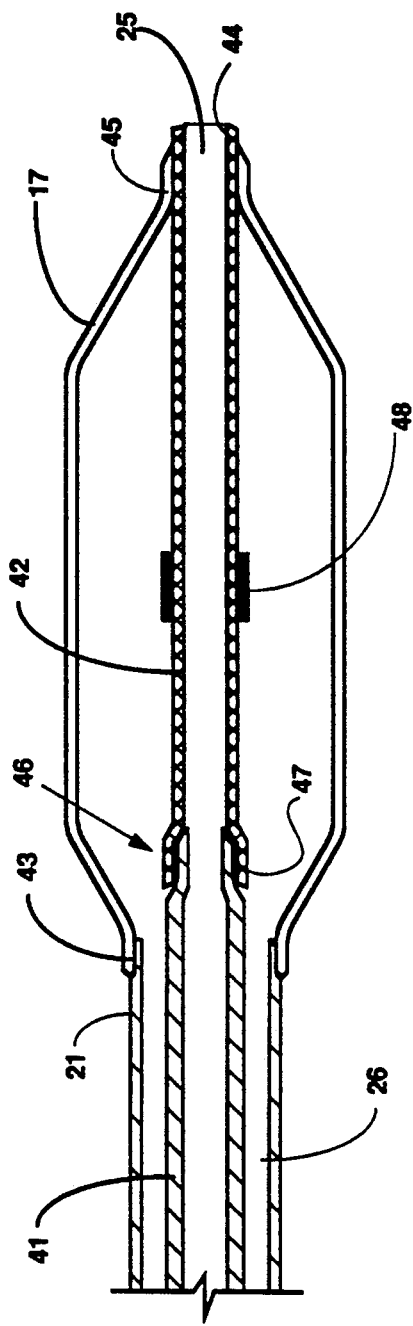
FIG. 3 is a longitudinal cross section of the distal end of a catheter body, including catheter shaft, balloon and inner tubular element in accordance with the present invention.

FIG. 3 is an enlarged view of the distal end of the catheter component, showing the balloon 17, a portion of the outer tubular element 21, and the two segments 41, 42 of the inner tubular element. The balloon 17 is preferably polyethylene terephthalate and the outer tubular element 21 is preferably flexible polyester such as Hytrel, Pebax, or a polyurethane. The two are bonded together at a fluid-tight joint 43 by a conventional adhesive (not shown). The two segments of the inner tubular element are the proximal, lubricious segment 41 and the distal, less lubricious but more readily bondable segment 42. In a presently preferred construction, the lubricious segment 41 is high density polyethylene with an inner diameter of 0.017 inch (0.043 cm), and an outer diameter of 0.022 inch (0.056 cm), and the distal segment 42 is Pebax with an inner diameter of 0.016 inch (0.041 cm) and an outer diameter of 0.025 inch (0.064 cm). The distal end 44 is bonded to the inside of the balloon orifice 45 by a conventional adhesive as described above (not shown), thereby permitting the guidewire to pass through the length of the catheter and out the distal end of the balloon while remaining sealed off from the inflation lumen 26 and the balloon interior. The distal segment 42 of the inner tubular element overlaps the proximal segment 41 at the joint 46, with the afore-mentioned adhesive 47 securing the two segments together. A radiopaque marker 48 encircles the distal segment inside the balloon to provide a means of tracking the catheter during its placement across a stenosis.

The foregoing description is offered primarily for purposes of illustration. It will be readily apparent to those skilled in the art that the construction of the system, the materials, the type, arrangement and location of components, and other parameters of the system may be further modified or substituted in various ways without departing from the spirit and scope of the invention.

What is claimed is:

1. In a catheter body for use in an over-the-wire catheter guidewire system in conjunction with a guidewire having a terminal segment whose exterior is other than a smooth metallic surface, said catheter body comprising an outer tubular member terminating in a balloon formed of a material selected from the group consisting of polyethylene terephthalate, nylon, and combinations thereof, and an inner tubular member defining an inflation lumen between said inner tubular member and said outer tubular member and a guidewire lumen inside said inner tubular member for advancement over said guidewire, said inner tubular member extending substantially the length of said outer tubular member and terminating at an orifice at the distal end of said balloon, said orifice sealed around said inner tubular member to isolate said balloon from said guidewire lumen, the improvement in which said inner tubular member is comprised of a proximal segment formed entirely of a lubricious polymer joined to a distal segment formed entirely of a material selected from the group consisting of polyamide-based polymers, polyurethane-based polymers and blends of a polyamide and a polyurethane, the length of said distal segment being less than the length of said terminal segment of said guidewire.

2. A catheter body in accordance with claim 1 in which said lubricious polymer is a polyolefin.

3. A catheter body in accordance with claim 1 in which said lubricious polymer is polyethylene.

4. A catheter body in accordance with claim 1 in which said polyamide-based polymer is a member selected from the group consisting of nylons, polyether-based polyurethanes, and blends of a polyamide and a polyether-based polyurethane.

5. A catheter body in accordance with claim 1 in which said polyamide-based polymer is a blend of a nylon and a polyether-based polyurethane.

6. A catheter body in accordance with claim 1 in which said polyamide-based polymer is a blend of a nylon and a polyurethane.

7. A catheter body in accordance with claim 1 in which said proximal and distal segments of said inner tubular member are joined at a joint located within said balloon.

8. A catheter body in accordance with claim 1 in which said proximal and distal segments of said inner tubular member are joined by overlapping facing ends of each.

9. A catheter body in accordance with claim 1 in which said proximal and distal segments of said inner tubular member are joined by overlapping facing ends of each, and by bonding said overlapping facing ends to each other by an adhesive.

10. A catheter body in accordance with claim 1 in which said proximal and distal segments of said inner tubular member are joined by overlapping facing ends of each, and by shrink fitting one of said overlapping facing ends over the other.

* * * * *